United States Patent [19]
Arndt et al.

[11] Patent Number: 5,949,550
[45] Date of Patent: Sep. 7, 1999

[54] METHOD AND APPARATUS FOR DETECTING DEFECTS IN A MOVING WEB

[75] Inventors: William A. Arndt, Wisconsin Rapids, Wis.; Robert C. Cibuzar, Minneapolis, Minn.; Randall A. Freeh, Wisc. Rapids, Wis.

[73] Assignee: Consolidated Papers, Inc., Wisconsin Rapids, Wis.

[21] Appl. No.: 08/915,982

[22] Filed: Aug. 21, 1997

[51] Int. Cl.⁶ .................................................. C01N 21/89
[52] U.S. Cl. ............................................................ 356/430
[58] Field of Search .................................. 356/429, 430, 356/446

[56] References Cited

U.S. PATENT DOCUMENTS

| | | |
|---|---|---|
| 3,763,483 | 10/1973 | Urmenyl . |
| 3,856,414 | 12/1974 | Menary ..................................... 356/430 |
| 4,160,913 | 7/1979 | Brenholdt ................................. 356/431 |
| 4,184,770 | 1/1980 | Pinior ....................................... 356/430 |
| 4,728,800 | 3/1988 | Surka ........................................ 356/430 |
| 4,760,271 | 7/1988 | Brenholdt ................................. 356/430 |
| 4,851,696 | 7/1989 | West ......................................... 356/430 |
| 4,883,233 | 11/1989 | Saukkonen et al. . |
| 4,921,183 | 5/1990 | Saukkonen et al. . |
| 5,064,131 | 11/1991 | van Biesen et al. . |
| 5,115,144 | 5/1992 | Konishi et al. . |
| 5,260,583 | 11/1993 | Rye ........................................... 356/430 |

FOREIGN PATENT DOCUMENTS

| | | |
|---|---|---|
| 3-255946 | 11/1991 | Japan . |
| 4-31755 | 2/1992 | Japan . |
| 3-255945 | 11/1994 | Japan . |

OTHER PUBLICATIONS

"Omron Luster Sensor E–3X–NL", Omron Electronics, Inc., Schaumburg, IL, date unknown.

"Reyco's 3160 Edge Marking System marks the edge with up to six colors of FDA certified dye.", Reyco, Inc., Marietta, GA, date unknown.

*Primary Examiner*—Richard A. Rosenberger
*Attorney, Agent, or Firm*—Juettner Pyle Piontek & Underwood

[57] ABSTRACT

A method and apparatus for detecting patches or areas of relatively high gloss on a moving web, and thereby associated wrinkles or other defects, and signalling the presence thereof comprises an analog and/or digital optical reflectivity sensor for sensing gloss on the surface of the moving web, a web marking device adjacent the edge of the moving web for marking the edge of the web with a dye, and a microcomputer for receiving the output signal from the sensor(s) and for controlling the operation of the marking device. The apparatus may also include a warning device such as a light or horn. The apparatus and method have particular applicability in association with paper web re-reeling equipment.

21 Claims, 4 Drawing Sheets

METHOD AND APPARATUS FOR DETECTING DEFECTS IN A MOVING WEB

BACKGROUND OF THE INVENTION

The present invention relates to methods and apparatus for detecting the presence of areas in the web where defects in moving paper webs, and in particular relates to a method and apparatus for detecting crepe wrinkles during paper re-reeling operations.

Defects in paper webs commonly occur during reeling operations. Such defects include crepe wrinkles, burst wrinkles and other weakened conditions in the web. The paper containing such wrinkles or other defects must be removed. Failure to remove the defective paper will likely cause web breaks during subsequent processing of the web.

At the end of a modern paper making machine, the paper is reeled at high speed onto a spool. It has been found that crepe wrinkles most commonly occur radially near the spool of the paper machine reel. From the paper machine, the paper reel is transported to a re-reeler. The re-reeler comprises an unwind station and a rewind station. When the web is re-reeled, crepe wrinkles that were near the spool of the original paper reel will be near the outer surface of the re-reeled reel. An operator may then remove or "slab off" paper containing crepe wrinkles and other defects. Paper may be slabbed off by manually cutting with a knife radially into the reel and across the reel. The slabbed off paper is unsuitable for sale.

A long standing problem in the industry i s accurately gauging how much paper should be slabbed off from the re-reeled reel. Because of high re-reeling speeds, the re-reeling crew often cannot accurately determine the location of crepe wrinkles or other defects. If the crew slabs off too little, defects will remain in the reel, which are likely to cause web breaks during later processing. If too much paper is slabbed off, it will result in a waste of saleable paper.

Various devices have been devised to detect wrinkles and other defects in moving paper webs. For example, U.S. Pat. No. 3,763,483 discloses an apparatus for mechanically "feeling" creases, bumps and other discontinuities in the surface of a moving web. U.S. Pat. Nos. 4,184,770 and 4,851,696 disclose devices that direct laser beams at or near the surface of a moving web. Variations in light received by a photoelectric sensor indi cate discontinuities, e.g., wrinkles, in the surface of the web. U.S. Pat. No. 4,160,913 scans the surface of the web with a small, rectangular "flying spot" light source. A detector receives reflected illumination. A hole in the web gives lower reflected illumination, while a wrinkle gives a higher than average illumination.

A draw back to the prior art devices is that each is designed to detect the presence of a wrinkle or defect itself. Since such defects are commonly very small, the surface area of the web relatively large, and the speed of the web fast, it exceedingly difficult to reliably detect defects. Invariably, the prior art detection equipment is either very sophisticated and expensive on the one hand, or unreliable on the other.

Accordingly, there is a long standing but unresolved need in the industry for a simple, inexpensive method and apparatus for reliably detecting crepe wrinkles and other associated defects and for accurately marking the location of the defective paper.

SUMMARY OF THE INVENTION

At a paper machine reel, crepe wrinkles occur radially near the spool and near the edges of the web. Specifically, the wrinkles are typically within six inches in a radial direction outwardly from the spool, and are within about 2.5 feet from the edge of the web in a cross machine direction, although these dimensions may vary depending on machine width and spool stiffness. Further, it has been discovered that the paper surface adjacent wrinkles has a higher than normal gloss level associated therewith. The gloss patches commonly have a gloss value of 5 to 20 points (standard TAPPI gloss units) higher than normal. These high gloss patches may be from several inches to a foot or more in length in the machine direction, and run generally the length of the wrinkle in the cross machine direction. The high gloss patches thus have a relatively large surface area, typically a square foot or more. The high gloss patches are commonly found, in the direction of web travel on the re-reeler, in front of the wrinkle on the felt side of the web. Gloss patches have been noted on the wire side as well. Gloss patches have been observed in front of and behind wrinkles, in the direction of web travel on the re-reeler. The exact technical cause for the formation of the high gloss patches is not known, but it is believed to be caused by slippage of the web near the spool during reeling, which results in a calendering action on the web surface. The same phenomenon that causes crepe wrinkles likely contributes to the formation of the observed gloss patches.

A method and apparatus for detecting patches or areas of relatively high gloss, and thereby detecting areas in which wrinkles or other defects, and signalling the presence of such high gloss patches is a primary object of the invention. A preferred embodiment of the apparatus of the invention comprise a sensor means for sensing gloss on the surface of the moving web, a marking means adjacent the edge of the moving web and downstream from said sensor means for marking the web, and a microcomputer for receiving the output signal from the sensor means and for controlling the operation of the marking means. The sensor means is preferably an optical, reflectivity sensor positioned about 18 inches inwardly from the edge of the moving web in the cross-machine direction. The apparatus may also include a warning device such as a light or horn.

A preferred method of the invention comprises the steps of monitoring the gloss level of the paper with the sensor means, establishing a normal gloss level range with the microcomputer, and upon detection of a gloss level exceeding the establishes range by a predetermined amount, activating the marking means to mark the edge of the web. The microcomputer also activates the warning light or horn.

The resultant paper reel will have a dye mark on the reel edge corresponding to each gloss spot. Since the gloss patches are associated with wrinkles and other defects, removal of the paper containing the gloss patches will result in removal of the wrinkles or other defects. Thus, the operators may accurately slab off the paper containing the defects without unnecessary waste.

The method and apparatus of the invention further includes correlating the occurrence of high gloss patches with unwind reel position data and other machine operating data. The resultant database can be used for trouble shooting purposes.

It is important to recognize that unlike prior art systems, the method and apparatus of the invention does not detect the wrinkle or defect per se. Prior art systems detect physical characteristics of wrinkles or other defects. As the wrinkles are often very small, typically 0.1 inch or less in width in the machine direction, the detection apparatus must be very sensitive and discriminating, or risk failure to accurately detect wrinkles.

The present invention overcomes these problems by detecting the relatively large gloss patch associated with the wrinkle, not the wrinkle itself. The high gloss patch typically extends for six to twelve inches in the machine direction, and is, therefore, many times larger than the wrinkle. Accordingly, the high gloss patch may be more reliably detected with relatively inexpensive, commercially available equipment.

Other attributes and benefits of the present invention will become apparent from the following detailed specification when read in conjunction with the accompanying drawings.

DETAILED DESCRIPTION

Figure 2:
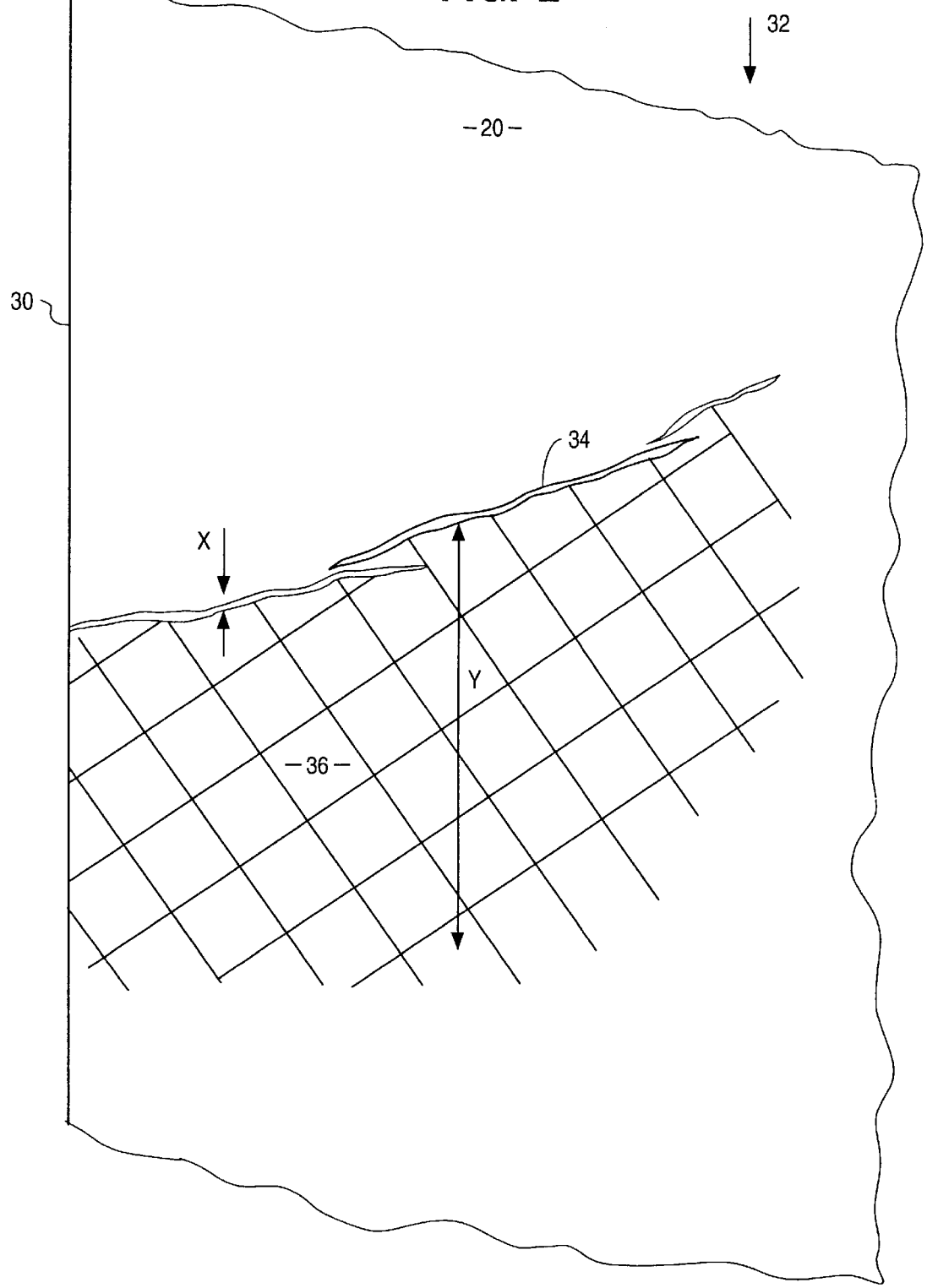
FIG. 2 is plan view of a surface of a paper web showing a crepe wrinkle and an associated high gloss patch.
Figure 3A:
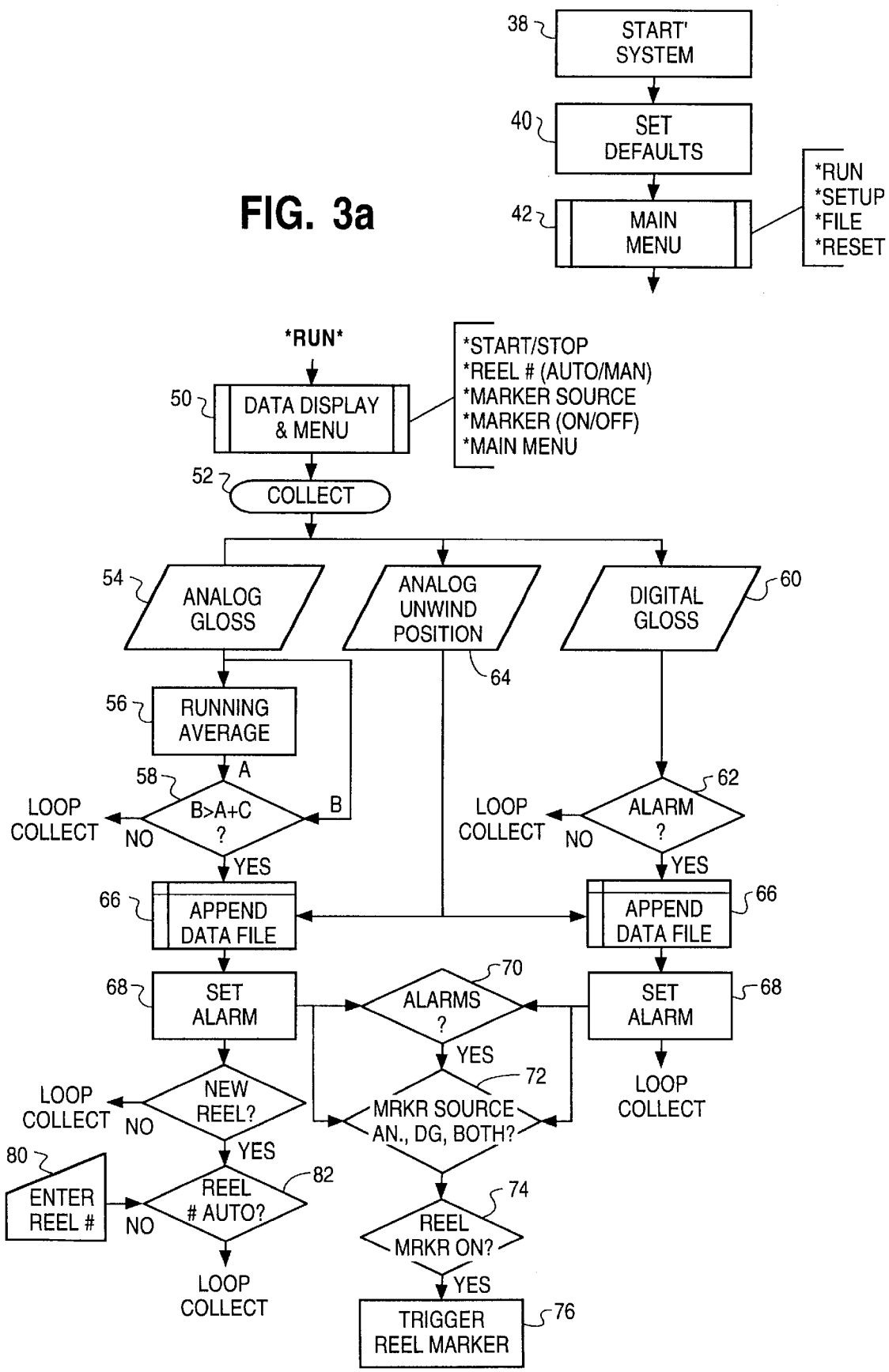
FIG. 3 is a flow chart showing a preferred process of the invention.
Figure 3B:
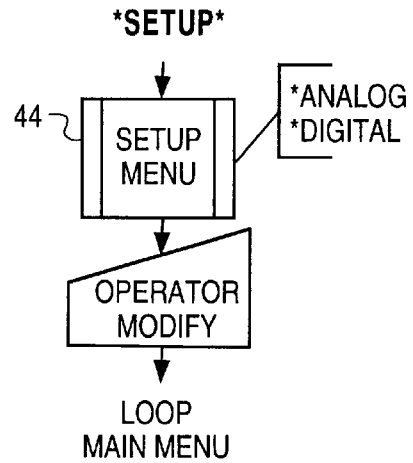
Figure 3B:
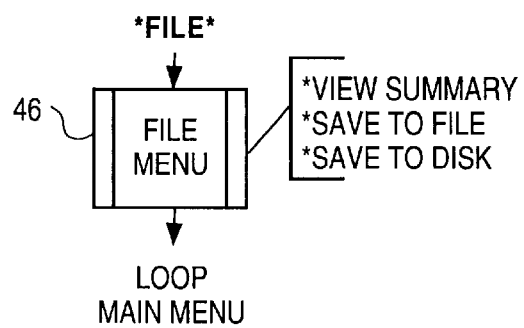
Figure 3B:
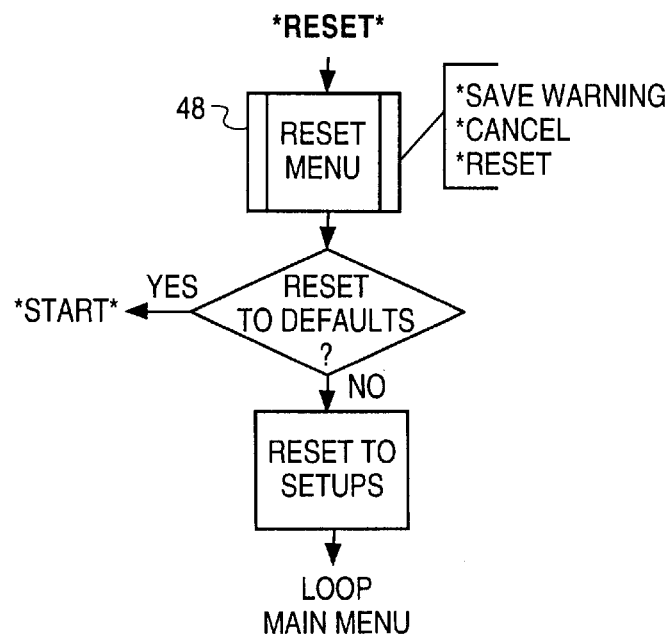

Turning now to the drawings, FIG. 2 illustrates the felt side surface of a paper web 20 having edge 30, moving in a machine direction 32 on a re-reeler. A crepe wrinkle 34 appears on the web, with an associated high gloss area 36 indicated by crosshatching. Crepe wrinkles typically appear at or near the edge 30 of the web, and extend at an angle in the cross machine direction. In severe cases, crepe wrinkles may extend all the way across a web, but commonly extend about 2 feet in the cross machine direction. The wrinkle 34 has a width X in the machine direction of about 0.1 inch, and may be less.

The high gloss area 36 is adjacent the wrinkle 34. On the felt side of the web, the gloss area typically is in front of the wrinkle in the re-reeler machine direction and parallels the length of the wrinkle in the cross machine direction. The high gloss patch characteristically has a dimension Y in the machine direction of about 6 to 12 inches. Accordingly the high gloss area 36 has a machine direction dimension Y that is more than 50 times greater than the wrinkle itself X. Typically, enamel coated light weight publication grade papers, before calendering, have a gloss value of about 10–15 points, standard TAPPI gloss units. The high gloss patches typically have gloss values of 20 to 30 points.

Figure 1:
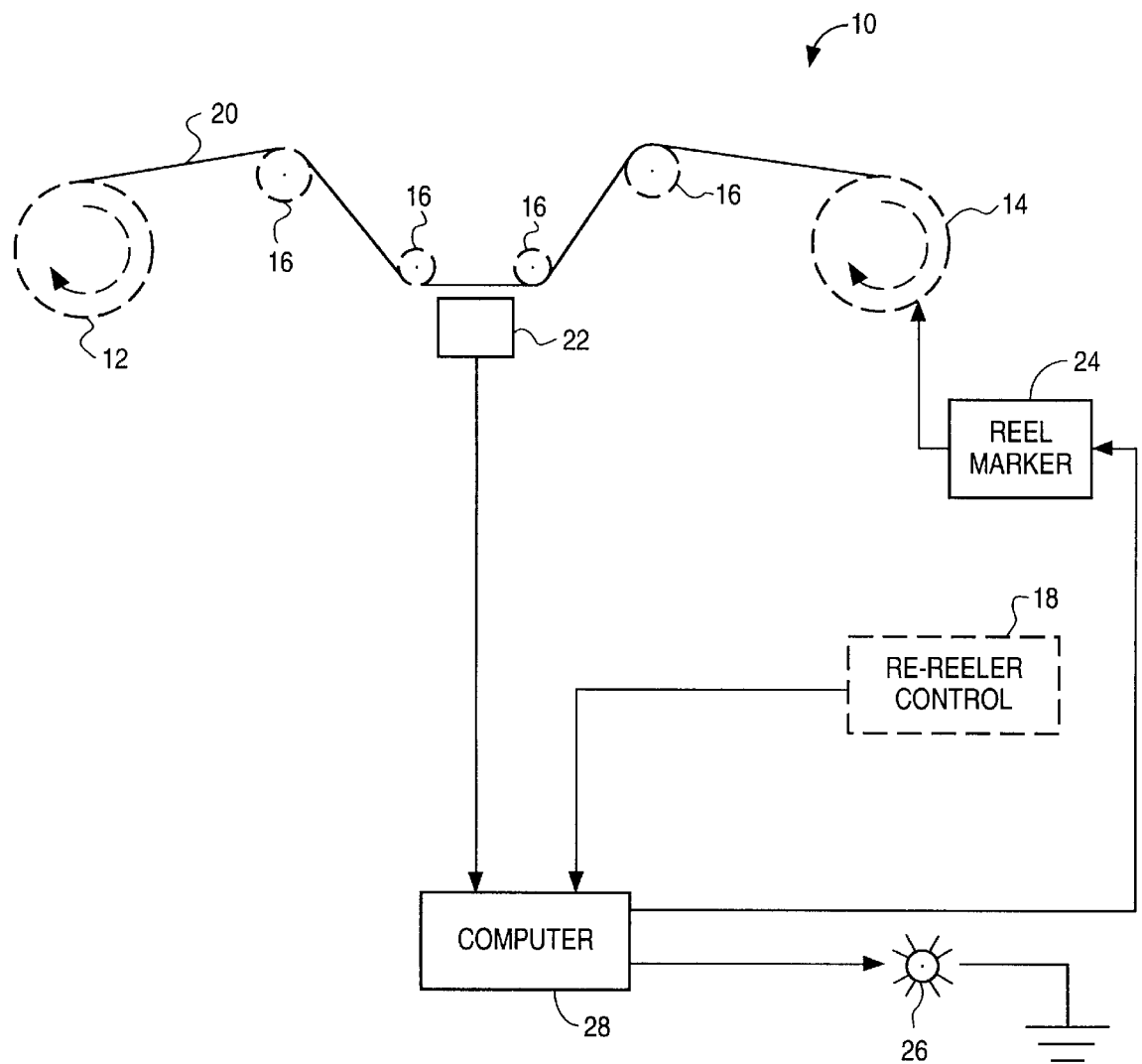
FIG. 1 is a schematic illustration of a re-reeler showing the apparatus of the invention.

Turning now to FIG. 1 of the drawings, a paper re-reeler, indicated generally at 10, is shown schematically in phantom lines. The re-reeler 10 comprises an unwind station 12, a winder 14, guide rolls 16, and a re-reeler control 18. A web 20 is unwound from the unwind station 12, passes over guide rolls 16 and is rewound at winder 14. Re-reelers are conventionally used to prepare paper reels for further processing, for example, to remove web defects before supercalendering, and to trim the reel width. Re-reeling equipment and the operation thereof is well known to those skilled in the art.

The apparatus of the invention comprises at least one optical sensing means 22, a reel marking means 24, a warning indicator 26 and computer 28. The sensing means may be any device capable of measuring gloss on the surface of a moving web. Optical reflectivity sensors have been found to work well. One or more sensors 22 are mounted adjacent the surface of the moving web at location(s) in the cross machine direction where wrinkles or other defects are anticipated. In particular, it has been found that an operative location for a sensor is between 6–24 inches inwardly in the cross machine from the edge of the web. A preferred location is about 18 inches inwardly from the edge of the web. An analog optical reflectivity sensor found to work well is a Hunter glossmeter, manufactured by Hunter Associates Laboratory, Inc., Reston, Va. A digital optical reflectivity sensor that is acceptable is Omron Lustor Sensor E3X-NL available from Omron Electronics, Inc., Schaumberg, Ill.

The reel marking means 24 may be any device capable of marking the edge of a moving paper web or roll. The marking means is mounted to the re-reeler framework down machine from the sensing means. One suitable marking means is Ryeco 3160 Edge Marking System, manufactured by Ryeco, Inc., Marietta, Ga. The Ryeco Edge Marking System marks the edge of the web or paper roll by spraying a colored or black dye on the edge of the moving web. The marking device is preferably activated automatically with the detection of a high gloss patch, but in addition or alternatively, could be activated manually by the machine operator.

A warning indicator 26 is shown as a lamp, but could be any form of a visual, audible or other warning device, for example a horn.

A computer 28 receives inputs indicating gloss values from the sensor means and web or reel position from the re-reeler control. It is preferably a conventional micro computer, but could be a programmable controller. It may be programmed in any manner, as is well known in the art, to perform the above described functions.

A flow chart from which one skilled in the art may program such functions is illustrated diagrammatically in the FIG. 3. The program is designed for a system employing both analog and digital optical sensors. The first function is to start the system 38, set default parameters 40 and bring up the main menu 42. The main menu includes program options: run, setup, file and reset.

The setup routine 44 permits the operator to set the programmable parameters for the system sensors. In the illustrated embodiment, the system includes both analog and digital optical reflectivity sensors.

The file routine 46 allows the operator to review, save, output or otherwise utilize stored data. The reset routine 48 functions to reset the system before a new paper reel is rewound or after a web break. The operator may choose from the save warning, cancel or reset options.

The run routine 50 controls the operation of the wrinkle or defect detection system. A Data Display & Menu 50 includes functions that allow the operator to start or stop the system. Menu 50 further permits a reel number to be manually entered. Otherwise, the system will automatically assign a sequential number. The Menu 50 also allows the operator to activate the analog sensor, digital sensor or both sensors.

When the detection system of the invention is started, the sensing means begins to collect data. The analog sensor 54 will provide continuous quantitative gloss data. The program at loop 56 will compute a run average gloss value "A." An incoming gloss value "B" exceeding the run average by a more than a predetermined value "C," indicates the presence of high gloss patch, and the marking system will be activated. Since the gloss patch will typically have a gloss level of 5 to 20 points higher than the normal sheet, the value "C" may be set at about 5 to 10 points, standard TAPPI gloss units. The actual value "C" selected will depend on specific operating conditions and should be low enough to avoid missing defects, but high enough to avoid false readings resulting from normal gloss variations.

The digital gloss meter 60 is preset to trigger a signal when the gloss level exceeds a preset value. Accordingly, run averaging is not necessary. For example, on a coated, uncalendered publication grade, the normal gloss level of the web is in the range of 10–15 points, standard TAPPI gloss units, the gloss patches are in the range of 20–30 points. Under these conditions, the digital gloss meter should be set to signal on detection of gloss levels a between 15 and 20 points or above. If the digital sensor is preset at a gloss level that is too high, it will potentially miss some web defects. Correspondingly, if set too low, it may trigger false alarms. For these reasons, it can be advantageous to utilize both sensor types for their particular benefits.

When a high gloss patch has been detected, by either type of sensor, a data record 66 is made that includes the gloss data input from the sensors plus the reel unwind position 64 received from the re-reeler control 18. An alarm 70 is triggered. Next, the system will check the designated marker source 72, analog, digital or both. If the marker source is satisfied, the system will check (at 74) whether the reel marker is on, and if so the program will trigger the reel marker 76.

The running average for the analog sensor will be recalculated for each new reel. If the sensor detects a new reel 78, the program will clear the running average and will permit a new reel number to be added manually 80. If no new reel number is entered, the system will automatically assign a sequential number 82.

For each high gloss patch detected, a data record is preferably made. The data is preferably compiled in a reel summary report. The report may include for each high gloss patch encountered ("alarm") the reel number, grade and basis weight of the paper, alarm number, unwind reel position (radial thickness of paper remaining on the reel), analog gloss value for the alarm, running average gloss value, and windup reel position (radial thickness of paper on the reel). It is also beneficial to record the finished reel diameter, and compute the radial distance from the first alarm to the top of the reel. The later figure reflects the amount of paper that should be slabbed off the reel. The collected reel data may be further combined with operational data from earlier processing, i.e., the paper machine reel, to help ascertain the cause of and prevent further crepe wrinkle formation.

The foregoing description and drawings illustrate and describe the method and apparatus of the invention in the context of re-reeling equipment. However, it should be understood that the method and apparatus of the invention may be used in a variety of other contexts. For example, the invention could be advantageously used on the unwinds of off line coaters, calenders, supercalenders, converting equipment and finishing winders. In addition, the invention may have applicability in the printing industry on various types of printing presses, including web offset and rotogravure presses.

While the preferred embodiment of the present invention has been shown and described, it is to be understood that various modifications and changes could be made thereto without departing from the scope of the appended claims.

What is claim is:

1. A method for detecting defects in a moving web, comprising the steps of:
   providing a sensor means near the edge of the moving web for sensing gloss on the surface of the moving web;
   providing a signaling means for signaling a web defect;
   sensing the web with the sensor means for detecting patches of relatively high gloss on the surface of the web; and
   activating the signaling means to signal a web defect upon detection of a patch of relatively high gloss.

2. A method as in claim 1, wherein the sensor means comprises an optical reflectivity sensor.

3. A method as in claim 1, wherein the sensor means provides a output signal indicating the gloss level of the web surface.

4. A method as in claim 1, wherein the sensor is located within 2.5 feet of the edge of the web in a cross machine direction.

5. A method as in claim 1, wherein the signaling means comprises a marking means adjacent the edge of the moving web and activated by the sensor means for marking the edge of the moving web at the location on the web of a patch of relatively high gloss.

6. A method as in claim 5 wherein the marking step comprises spraying a dye on edge of the moving web.

7. A method as in claim 1 wherein the signaling means comprises an alarm activated by the sensing means upon detection of a patch of relatively high gloss.

8. A method as in claim 1, wherein the sensor means provides a continuous output signal, further comprising the steps of
   providing a microcomputer for receiving the output signal from the sensor means;
   continuously monitoring the gloss level of the moving web with the microcomputer to establish an average running gloss value for the web; and
   generating a signal from the microcomputer to the signaling means upon detection by the sensor means of a gloss level exceeding by a predetermined value the average running gloss value to activate the signaling means.

9. A method as in claim 8, further comprising the steps of gathering machine operating data and generating a database of gloss level and machine operating data.

10. A method as in claim 9, wherein the machine operating data includes web or reel position data.

11. A method as in claim 1, further comprising the step of generating a reel summary report that includes the number and position of gloss patches.

12. A method of detecting defects in a moving web on a re-reeler, comprising the steps of
   providing a sensor means for sensing gloss on the surface of the moving web;
   positioning the sensor means near the edge of the moving web in the cross-machine direction;
   providing a marking means adjacent the edge of the moving web for marking the web;
   providing a microcomputer for receiving the output signal from the sensor means and for controlling the operation of the marking means;
   sensing gloss level of the moving web with the sensor means;
   transmitting gloss level data to the microcomputer;
   determining an occurrence of a gloss patch of at least several inches in length in the machine direction having a gloss level exceeding a predetermined value; and
   marking the edge of the moving web upon occurrence of gloss patches having a gloss level that exceeds the predetermined value.

13. A method as in claim 12, wherein the marking step comprises spraying a dye on edge of the moving web.

14. A method as in claim 12 further comprises the step of activating an alarm when the gloss level exceeds the predetermined value.

15. An apparatus for detecting defects in a moving web, comprising sensor means mounted near the edge of the moving web for sensing gloss on the surface of the moving web;

discerning means responsive to said sensor means for discerning a gloss patch of at least several inches in length in the machine direction and having a gloss level higher than a predetermined value, and for providing an output signal upon discerning a said gloss patch having a gloss level higher than said predetermined value; and signaling means responsive to the output signal of said discerning means for signaling a web defect.

16. An apparatus as in claim 15, wherein said sensor means and said discerning means comprises a digital, optical reflectivity sensor preset to said predetermined value.

17. An apparatus as in claim 15, wherein said sensor means is an analog optical reflectivity sensor and said discerning means is a microprocessor programmed to establish an average running gloss value for the web and to discern gloss values higher than the computed average.

18. An apparatus as in claim 17, wherein said sensor means further comprises a digital optical reflectivity sensor preset to said predetermined value.

19. An apparatus as in claim 15, wherein said signalling means comprises a web edge marker adjacent the edge of the moving web.

20. An apparatus as in claim 15, wherein said signalling means comprises an alarm.

21. An apparatus for detecting defects in a moving web on a re-reeler having a unwind station and a winder, comprising an optical reflectivity sensor mounted near the edge of the moving web in the cross-machine direction between the unwind station and the winder for sensing the gloss level of the surface of the edge portion of the web and for providing a gloss level output signal;

a web edge marker mounted to the winder adjacent the edge of the web; and a microcomputer receptive of the output signal from said sensor and upon the occurrence of a gloss patch of about 6 to 12 inches in length in the machine direction, the patch having a gloss level exceeding a predetermined value, providing an output signal to control the operation of said marking means for marking the edge of the web at the location of the gloss patch.

* * * * *